(12) United States Patent
Wenger et al.

(10) Patent No.: US 8,283,497 B2
(45) Date of Patent: Oct. 9, 2012

(54) TRICYANOBORATES

(75) Inventors: Wolfgang Wenger, Visp (CH); Cornelia Zur Taschler, Termen (CH)

(73) Assignee: Lonza Ltd., Visp (CH)

( * ) Notice: Subject to any disclaimer, the term of this patent is extended or adjusted under 35 U.S.C. 154(b) by 0 days.

(21) Appl. No.: 13/147,416

(22) PCT Filed: Jan. 26, 2010

(86) PCT No.: PCT/EP2010/000426
§ 371 (c)(1),
(2), (4) Date: Aug. 2, 2011

(87) PCT Pub. No.: WO2010/086131
PCT Pub. Date: Aug. 5, 2010

(65) Prior Publication Data
US 2012/0018676 A1    Jan. 26, 2012

Related U.S. Application Data

(60) Provisional application No. 61/151,224, filed on Feb. 10, 2009.

(30) Foreign Application Priority Data

Feb. 2, 2009    (EP) .................................... 09001388

(51) Int. Cl.
C07F 5/02    (2006.01)
(52) U.S. Cl. ........... 568/1; 252/62.2; 252/364; 423/277; 423/284; 423/364; 423/385; 568/18

(58) Field of Classification Search ................. 252/62.2, 252/364; 568/1, 18; 423/277, 284, 364, 423/385
See application file for complete search history.

(56) References Cited

U.S. PATENT DOCUMENTS

| 7,645,434 B2 | 1/2010 | Welz-Biermann et al. |
| 2007/0293391 A1 * | 12/2007 | Finze et al. .................. 502/154 |

FOREIGN PATENT DOCUMENTS

| DE | 10 2004 051278 A1 | 4/2006 |
| WO | 2004/072089 A1 | 8/2004 |
| WO | WO2012041434 | * 4/2012 |

OTHER PUBLICATIONS

Bessler, et al., "Preparation of some cyanoboron compounds," Z. Anorg Allg. Chem., 1967, 352, No. 1-2, pp. 67-76.
Yao, et al., "Organo-Tricyanoborates as Tectons: Illustrative Coordination Polymers Based on Copper(I) Derivatives," Inorg. Chem., 2005, 44, No. 18, pp. 6256-6264.

* cited by examiner

*Primary Examiner* — Mark Kopec
*Assistant Examiner* — Haidung Nguyen
(74) *Attorney, Agent, or Firm* — McDonnell Boehnen Hulbert & Berghoff LLP

(57) ABSTRACT

The present invention relates to novel tricyanoborates of the general formula $Cat^{n+}[B(CN)_3(XR^1)]^-{}_n$, wherein $R^1$ is $C_{1-6}$ alkyl, $C_{2-6}$ alkenyl, $C_{6-10}$ aryl or benzyl; X is oxygen or sulfur; and $Cat^{n+}$ is a cation with n being 1 or 2, which is selected from the group consisting of an inorganic cation and an organic cation; and also their preparation and use.

33 Claims, No Drawings

TRICYANOBORATES

This application is a US national phase of International Application No. PCT/EP2010/000426 filed on Jan. 26, 2010, which claims the benefit of European patent application 09001388.9, filed Feb. 2, 2009 and U.S. patent application Ser. No. 61/151,224, filed Feb. 10, 2009, the disclosures of which are incorporated herein by reference in their entirety.

The present invention relates to novel tricyanoborates, their use and processes for preparing them.

The term "ionic liquids" is usually used to refer to salts which are liquid at temperatures below 100° C., in particular at room temperature. Such liquid salts typically comprise organic cations and organic or inorganic anions.

The organic cations of ionic liquids are usually quaternary ammonium or phosphonium ions or cations of aromatic, usually nitrogen-containing bases which may be substituted by alkyl groups, halogen atoms or cyano groups and may contain further heteroatoms such as phosphorus, sulfur or oxygen. Examples of customary organic cations are imidazolium, oxazolium, pyrazinium, pyrazolium, pyridazinium, pyrrolidinium, pyridinium, thiazolium and triazolium cations.

Typical anions in ionic liquids are $AlCl_4^-$, $AsF_6^-$, $BF_4^-$, $Br^-$, $CF_3SO_3^-$, $(CF_3)_2PF_4^-$, $(CF_3)_3PF_3^-$, $(CF_3)_4PF_2^-$, $(CF_3)_5PF^-$, $(CF_3)_6P^-$, $Cl^-$, $CN^-$, $SCN^-$, $FeCl_3^-$, $NO_3^-$, $PF_6^-$, pyruvate, acetate, oxalate or the tricyanomethane anion described in EP-A-1 634 867. In addition, WO 2004/072089 and WO 2007/093961 disclose cyanoborate anions of the general formula $[BF_n(CN)_{4-n}]^-$, wherein n is 0, 1, 2 or 3.

Ionic liquids have a series of interesting properties: Usually, they are thermally stable, relatively non-flammable and have a very low vapour pressure. In addition, they have very good solvent properties for numerous organic and inorganic substances. Owing to their ionic structure, ionic liquids also have interesting electrochemical properties, for example electrical conductivity which is often accompanied by a high electrochemical stability. Therefore, there is a fundamental need for new ionic liquids having a variety of properties which open up additional opportunities for their use.

It is an object of the present invention to provide novel stable compounds which can be used as ionic liquids or as precursors of ionic liquids, and also a process for preparing them. These compounds should be able to be disposed of in an environmentally friendly manner after use.

This object is achieved by the tricyanoborates according to claim 1, by their use according to claim 12 and by the processes for their preparation according to claims 13 and 14. Further preferred embodiments are the subject-matter of dependent claims.

The present invention relates to novel tricyanoborates of the general formula

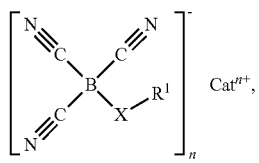 (I)

wherein $R^1$ is $C_{1-6}$ alkyl, $C_{2-6}$ alkenyl, $C_{6-10}$ aryl or benzyl, X is oxygen or sulfur, and
$Cat^{n+}$ is a cation with n being 1 or 2, which is selected from the group consisting of an inorganic cation $M^{n+}$ and an organic cation $Q^{n+}$ with n being 1 or 2.

Here and in the following, the expression "$C_{1-n}$ alkyl" refers to any linear or branched alkyl group which contains from 1 to n carbon atoms. For example, the expression "$C_{1-6}$ alkyl" encompasses groups such as methyl, ethyl, propyl, isopropyl, butyl, isobutyl, sec-butyl, tert-butyl, pentyl, isopentyl (3-methylbutyl), neopentyl (2,2-dimethyl-propyl), hexyl and isohexyl (4-methylpentyl).

Here and in the following, the expression "$C_{2-n}$ alkenyl" refers to a carbon chain which is made up of from 2 to n carbon atoms and contains at least one double bond, with the carbon atoms being saturated by hydrogen atoms and the carbon chain being able to be branched. For example, the expression "$C_{2-4}$ alkenyl" encompasses groups such as ethenyl, 1-methylethenyl, prop-1-enyl, prop-2-enyl, 2-methylprop-2-enyl and buta-1,3-dienyl.

Here and in the following, the expression "$C_{6-10}$ aryl" refers to an aryl group which has from 6 to 10 carbon atoms and may be substituted by one or more $C_{1-4}$ alkyl or $C_{1-4}$ alkoxy groups. For example, "$C_{6-10}$ aryl" encompasses phenyl, benzyl, methylphenyl, methoxyphenyl, dimethylphenyl, ethylmethylphenyl, diethylphenyl and naphthyl.

Tricyanoborates of formula I, wherein X is oxygen, are preferred.

Tricyanoborates of formula I, wherein $R^1$ is $C_{1-6}$ alkyl, preferably methyl, ethyl or propyl, and more preferably methyl, are also preferred.

In a further preferred embodiment, the cation $Cat^{n+}$ is an inorganic cation $M^{n+}$ with n being 1 or 2, which is selected from the group consisting of $Li^+$, $Na^+$, $K^+$, $Rb^+$, $Cs^+$, $NH_4^+$, $Be^{2+}$, $Mg^{2+}$, $Ca^{2+}$, $Sr^{2+}$ and $Ba^{2+}$.

In an also preferred embodiment, the cation $Cat^{n+}$ is an organic cation $Q^{n+}$ with n being 1 or 2, preferably with n being 1, which contains at least one heteroatom selected from the group consisting of nitrogen, phosphorus, sulfur and oxygen.

Particularly preferred are tricyanoborates of formula I which have a divalent organic cation $Q^{2+}$, such as, for example, ethylenediammonium.

Further particularly preferred are tricyanoborates of formula I which have a monovalent organic cation $Q^+$ selected from the group consisting of cations of formula (a) $(WR^2R^3R^4R^5)^+$, wherein W is a nitrogen or phosphorus, and
 (i) wherein $R^2$ to $R^4$ are, independently, $C_{1-20}$ alkyl, and $R^5$ is $C_{1-20}$ alkyl, $C_{3-10}$ cycloalkyl or $C_{6-10}$ aryl, wherein optionally $R^2$ to $R^5$, independently, contain one or more halogens, or
 (ii) wherein $R^2$ and $R^3$ together with W form a 5- to 7-membered ring and $R^4$ and $R^5$ are, independently, $C_{1-20}$ alkyl, wherein optionally $R^4$ and $R^5$, independently, contain one or more halogens, or
 (iii) wherein $R^2$ and $R^3$ or $R^4$ and $R^5$ in each case together with W form a 5- to 7-membered ring, or
(b) $(XR^6R^7R^8)^+$, wherein X is nitrogen and $R^6$ and $R^7$ together with X form a ring in which X formally has one single bond and one double bond to $R^6$ and $R^7$, and $R^8$ is $C_{1-20}$ alkyl, $C_{3-10}$ cycloalkyl or $C_{6-10}$ aryl, wherein $R^8$ optionally contains one or more halogens, or
(c) $(YR^9R^{10}R^{11})^+$, wherein Y is sulfur and
 (i) wherein $R^9$ and $R^{10}$ are, independently, $C_{1-20}$ alkyl and $R^{11}$ is $C_{1-20}$ alkyl, $C_{3-10}$ cycloalkyl or $C_{6-10}$ aryl, wherein optionally $R^9$ to $R^{11}$, independently, contain one or more halogens, or
 (ii) wherein $R^9$ and $R^{10}$ together with Y form a 5- to 7-membered ring and $R^{11}$ is $C_{1-20}$ alkyl, $C_{3-10}$ cycloalkyl or $C_{6-10}$ aryl, wherein $R^{11}$ optionally contains one or more halogens, or (d) $(ZR^{12}R^{13})^+$, wherein Z is oxygen or sulfur and $R^{12}$ and $R^{13}$ together with Z form a ring in which Z formally has one single bond and one double bond to $R^{12}$ and $R^{13}$, and wherein optionally one or more substituents selected from the group consisting of $C_{1-20}$ alkyl, $C_{1-20}$ alkoxy, $C_{3-10}$ cycloalkyl, $C_{6-10}$ aryl, halogen and cyano are bound to each of the rings formed with the substituents $R^2$ to $R^{13}$, wherein optionally the $C_{1-20}$ alkyl, the $C_{1-20}$ alkoxy, the $C_{3-10}$ cycloalkyl and the $C_{6-10}$ aryl, independently, contain one or more halogens, and wherein optionally each of the rings formed with the substituents $R^2$ to $R^{13}$ contains one or two further, substituted or unsubstituted heteroatoms selected from the group consisting of nitrogen, sulfur and oxygen and/or be fused to another aromatic or non-aromatic 5- to 7-membered ring. A suitable substituent of the heteroatom is, for example, $C_{1-8}$ alkyl.

Here and in the following, the expression "$C_{3-n}$ cycloalkyl" refers to a cycloalkyl group having from 3 to n carbon atoms. "$C_{3-10}$ cycloalkyl" represents, for example, cyclopropyl, cyclobutyl, cyclopentyl, cyclohexyl, cycloheptyl, cyclooctyl, cyclononyl or cyclodecyl.

Here and in the following, the expression "$C_{1-n}$ alkoxy" refers to an unbranched or branched alkoxy group having from 1 to n carbon atoms. "$C_{1-20}$ alkoxy" represents, for example, methoxy, ethoxy, propoxy, isopropoxy, butoxy, isobutoxy, sec-butoxy, tert-butoxy, pentyloxy, 1,4-dimethylpentyloxy, hexyloxy, heptyloxy, octyloxy, 1,5-dimethylhexyloxy, nonyloxy, decyloxy, 4-ethyl-1,5-dimethylhexyloxy, undecyloxy, dodecyloxy, tridecyloxy, tetradecyloxy or eicosyloxy.

Here and in the following, the expression "halogen" refers to fluorine, chlorine, bromine or iodine.

Particularly preferred are tricyanoborates of formula I with an organic cation $Q^+$ selected from the group consisting of organic ammonium, phosphonium, sulfonium, pyrrolidinium, pyrrolinium, pyrrolium, pyrazolium, imidazolium, triazolium, oxazolium, thiazolium, piperidinium, piperazinium, morpholinium, pyridinium, pyridazinium, pyrimidinium, pyrazinium, 1,3-dioxolium, pyrylium and thiopyrylium cation.

Preferably, the organic cation $Q^+$ is selected from the group consisting of

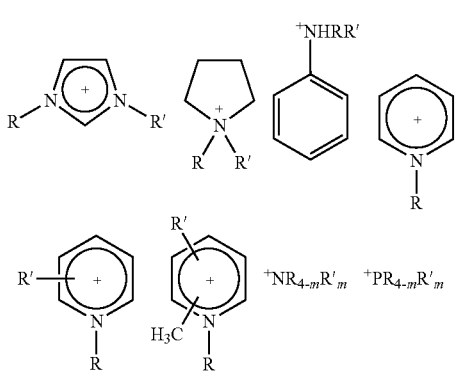

wherein R and R' are, independently, $C_{1-20}$ alkyl, preferably $C_{1-14}$ alkyl and more preferably $C_{1-8}$ alkyl, and m is an integer between 0 and 4. Favorably, the substituents R and R' have different lengths.

More preferably, the organic cation $Q^+$ is selected from the group consisting of

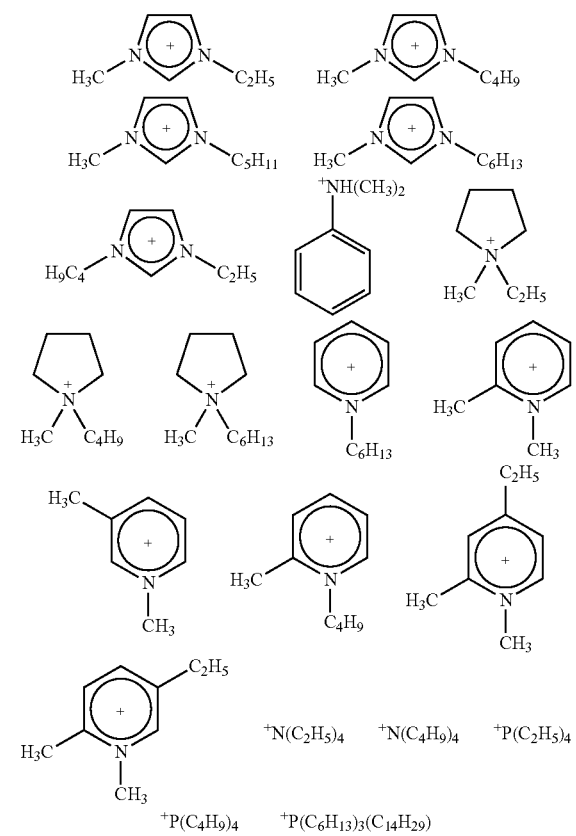

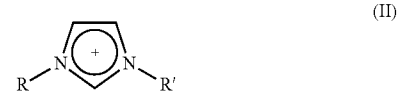

In a further particularly preferred embodiment, the organic cations $Q^+$ are imidazolium cations, in particular imidazolium cations of the general formula (II)

wherein R and R' are, independently, $C_{1-20}$ alkyl, preferably $C_{1-14}$ alkyl. In a most preferred embodiment, R is methyl and R' is ethyl.

In particular, the compound 1-ethyl-3-methylimidazolium tricyanomethoxyborate is claimed.

Tricyanoborates with an organic cation are usually liquid at temperatures below 100° C., in particular at room temperature, and are therefore referred to as ionic liquids. Owing to their property as ionic liquids, they are highly suitable as solvents for many organic and inorganic substances.

Therefore, claimed is the use of the tricyanoborate of formula I, wherein $R^1$ is $C_{1-6}$ alkyl, $C_{2-6}$ alkenyl, $C_{6-10}$ aryl or benzyl, X is oxygen or sulfur and $Cat^{n+}$ is an organic cation $Q^{n+}$ with n being 1 or 2, preferably with n being 1, optionally in a mixture with one or more other ionic liquids, water or organic solvents, as polar aprotic solvent.

Ionic liquids have many fields of use: They extend from the use as solvent in inorganic and organic synthesis through the use as electrolyte to release agents and/or additives for lubricants and hydraulic fluids. The spectrum of specific requirements which the ionic liquids have to meet in order to be suitable for a specific application is therefore correspondingly broad. The ionic liquids of the invention are characterized by, in particular, a non-coordinating anion. In addition, they are halogen-free, which makes inexpensive and environmentally friendly disposal possible, for example by incineration, and, owing to the low corrosivity towards metals, simplifies their use and storage.

The properties of the ionic liquids according to the invention can be varied by choice of suitable organic cations and suitable substituents —X—$R^1$ of the borate anion. Thus, for example, the melting point, the thermal and electrochemical stability, the viscosity, the polarity and the solubility in water or in organic solvents can be strongly influenced by variation of the substituents —X—$R^1$ of the borate anion and also by variation of the organic cation and its substituents.

Further, the present invention relates to a process for preparing the inorganic tricyano-borates of formula I, wherein $R^1$ is $C_{1-6}$ alkyl, $C_{2-6}$ alkenyl, $C_{6-10}$ aryl or benzyl, X is oxygen or sulfur and $Cat^{n+}$ is an inorganic cation $M^{n+}$ with n being 1 or 2, preferably selected from the group consisting of $Li^+$, $Na^+$, $K^+$, $Rb^+$, $Cs^+$, $NH_4^+$, $Be^{2+}$, $Mg^{2+}$, $Ca^{2+}$, $Sr^{2+}$ and $Ba^{2+}$, characterized in that
$B(XR^1)_3$ is reacted with a cyanotri-$C_{1-6}$-alkylsilane, in particular with cyanotrimethyl-silane (TMSCN), in the presence of $M^{n+}(CN^-)_n$, wherein
$R^1$ is $C_{1-6}$ alkyl, $C_{2-6}$ alkenyl, $C_{6-10}$ aryl or benzyl,
X is oxygen or sulfur, and
$M^{n+}$ is an inorganic cation with n being 1 or 2, preferably selected from the group consisting of $Li^+$, $Na^+$, $K^+$, $Rb^+$, $Cs^+$, $NH_4^+$, $Be^{2+}$, $Mg^{2+}$, $Ca^{2+}$, $Sr^{2+}$ and $Ba^{2+}$.

Preferably, $B(XR^1)_3$ and $M^{n+}(CN^-)_n$ are applied in a molar ratio of from 0.8:1.0 to 1.2:1.0, in particular in a molar ratio of from 0.9:1.0 to 1.1:1.0. The cyanotri-$C_{1-6}$-alkylsilane is preferably used in an excess based on $B(XR^1)_3$, for example in a molar ratio of from 1.5:1 to 10:1, in particular in a molar ratio of from 3:1 to 5:1. The process for preparing the inorganic tricyanoborates is preferably carried out at a temperature of from 0° C. to 250° C., in particular at a temperature of from 50° C. to 100° C. Preferably, the process for preparing the inorganic tricyanoborates is carried out at a temperature which is above the boiling point of the alkoxytri-$C_{1-6}$-alkylsilane formed as side product.

The present invention also relates to a process for preparing the organic tricyano-borates of formula I, wherein $R^1$ is $C_{1-6}$ alkyl, $C_{2-6}$ alkenyl, $C_{6-10}$ aryl or benzyl, X is oxygen or sulfur and $Cat^{n+}$ is an organic cation $Q^{n+}$ with n being 1 or 2, preferably n being 1, characterized in that
the inorganic tricyanoborates of formula I, wherein $R^1$ is $C_{1-6}$ alkyl, $C_{2-6}$ alkenyl, $C_{6-10}$ aryl or benzyl, X is oxygen or sulfur and $Cat^{n+}$ is an inorganic cation $M^{n+}$ with n being 1 or 2, preferably selected from the group consisting of $Li^+$, $Na^+$, $K^+$, $Rb^+$, $Cs^+$, $NH_4^+$, $Be^{2+}$, $Mg^{2+}$, $Ca^{2+}$, $Sr^{2+}$ and $Ba^{2+}$,
are reacted with a salt of formula $(Q^{n+})_p(Y^{p-})_n$, wherein
$Q^{n+}$ is an organic cation, in particular an organic cation containing at least one heteroatom selected from the group consisting of nitrogen, phosphorus, sulfur and oxygen,
n is 1 or 2,
$Y^{p-}$ is an anion selected from the group consisting of halides, pseudohalides, sulfate and organic acid anions and
p is 1 or 2.

In a preferred embodiment, the inorganic tricyanoborates used are prepared precedent according to the process for their preparation as claimed above.

The halide as anion $Y^-$ of the salt of the formula $(Q^{n+})(Y^-)_n$ can be selected from the group consisting of fluoride, chloride, bromide and iodide. Particularly preferred is chloride.

As pseudohalide anions $Y^-$ in the salt $(Q^{n+})(Y^-)_n$, anions which consist of at least two electronegative atoms and which are chemically similar to the halogens can be used. Preferably, the pseudohalide anion is selected from the group consisting of $CN^-$, $OCN^-$, $SCN^-$ and $N_3^-$. More preferably, the pseudohalide anion is $CN^-$.

Suitable examples for organic acid anions are anions of monobasic and dibasic non-aromatic and aromatic acids, such as acetate, oleate, fumarate, maleate, pyruvate, oxalate and benzoate. Particularly preferred are acetate and pyruvate anions.

When n and p are 1, and when n and p are 2, the inorganic tricyanoborate as defined above and the salt of the formula QY are preferably used in a molar ratio of from 0.8:1.0 to 1.2:1.0, in particular in a molar ratio of from 0.9:1.0 to 1.1:1.0.

The reaction is preferably carried out in a solvent or solvent mixture, for example in a two-phase solvent mixture comprising water and at least one organic solvent, for example in a mixture of water and methylene chloride. As an alternative, the reaction can also be carried out in the absence of a solvent or in an organic solvent in which the inorganic salt formed as side product is sparingly soluble or insoluble. As a further alternative, it is also possible to carry out the reaction in an aqueous solution using a previously loaded ion exchanger.

The process for preparing the organic tricyanoborates is preferably carried out at a temperature of from 10° C. to 250° C., in particular at a temperature in the range from room temperature to 100° C.

EXAMPLES

Abbreviations:
TMSCN=cyanotrimethylsilane
TMSOMe=methoxytrimethylsilane
EA=elemental analysis
CP-OES=optical emission spectrometry with inductively coupled plasma
br=broad Example 1

Synthesis of potassium tricyanomethoxyborate $K[B(CN)_3(OCH_3)]$ $B(OCH_3)_3$ (20.0 g, 0.19 mol) and KCN (12.5 g, 0.19 mol) were dissolved in TMSCN (66.8 g, 0.67 mol) and heated at a reflux temperature of 70° C. under protective gas for 18 hours. After cooling, all volatile components (unreacted TMSCN, formed TMSOMe) were distilled off to give powdery $K[B(CN)_3(OCH_3)]$ in a yield of 27.8 g (92%).

$^1$H-NMR (400 MHz, $CD_3CN$, TMS): δ [ppm]=3.22 (q, $J_{H/B}$=3.5 Hz, 3H).

$^{13}$C-NMR (125 MHz, $CD_3CN$, TMS): δ [ppm]=53.26 (s); 128.7 (q (80%)+septet (20%), q: J=69.9 Hz, septet: J=23.0 Hz).

$^{11}$B-NMR (160.3 MHz, $CD_3CN$, $BF_3.Et_2O$ external): δ [ppm]=−18.5 (s).

IR (Nujol): ν [$cm^{-1}$]=2228, 2163, 1201, 1221 br, 965, 926, 866.

Melting point: >240° C. (decomposition).

Analysis:

| Element | C | H | N | B | K |
|---|---|---|---|---|---|
| Method | EA | EA | EA | CP-OES | CP-OES |
| % expected | 30.22 | 1.90 | 26.43 | 6.80 | 24.29 |
| % found | 30.50 | 2.20 | 25.70 | 6.90 | 21.13 |

Example 2

Synthesis of 1-ethyl-3-methylimidazolium tricyanomethoxyborate (ionic liquid)

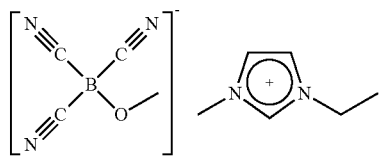

An aqueous solution of 1-ethyl-3-methylimidazolium chloride (5.0 g, 34 mmol), K[B(CN)$_3$(OCH$_3$)] (5.4 g, 34 mmol) and water (25.1 g) were mixed with methylene chloride (67 g) and stirred at room temperature for 1 hour. After separation of the aqueous and the organic phase, the organic phase was washed with 10 ml of water and evaporated on a rotary evaporator yielding 5.81 g (74%) of 1-ethyl-3-methylimidazolium tricyanomethoxyborate as a colorless, low-viscosity liquid which did not solidify even at a temperature of −10° C.

$^1$H-NMR (400 MHz, CD$_3$CN, TMS): δ [ppm]=1.62 (br t, J=7.0 Hz, 3H), 3.33 (q, J$_{H/B}$=3.5 Hz, 3H), 4.01 (s, 3H), 4.30 (br q, J=7.0 Hz, 2H), 7.36 (s, 1H), 7.39 (s, 1H), 8.67 (s, 1H).

$^{13}$C-NMR (125 MHz, CD$_3$CN, TMS): δ [ppm]=15.1 (s), 36.8 (br), 45.7 (s), 53.3 (s), 122.3 (br), 124.0 (br), 128.3 (q (80%)+septet (20%), q: J=69.9 Hz, septet: J=23.0 Hz).

Melting point: Below 0° C.

Example 3

Synthesis of 1-ethyl-3-methylimidazolium tricyanomethoxyborate (ionic liquid)

A solution of 1-ethyl-3-methylimidazolium chloride (5.0 g, 34 mmol) in water (25 ml) and K[B(CN)$_3$(OCH$_3$)] (5.4 g, 34 mmol) were mixed with methylene chloride (67 g) and stirred at room temperature for 3 hours. After separation of the aqueous and the organic phase, the latter was washed with 10 ml of water, dried over potassium carbonate and finally evaporated on a rotary evaporator yielding 3.78 g (48%) of 1-ethyl-3-methylimidazolium tricyanomethoxyborate as a low-viscosity liquid.

$^1$H-NMR (400 MHz, CD$_3$CN, TMS): δ [ppm]=1.62 (br t, J=7.0 Hz, 3H), 3.33 (q, J$_{H/B}$=3.5 Hz, 3H), 4.01 (s, 3H), 4.30 (br q, J=7.0 Hz, 2H), 7.36 (s, 1H), 7.39 (s, 1H), 8.67 (s, 1H).

$^{13}$C-NMR (125 MHz, CD$_3$CN, TMS): δ [ppm]=15.1 (q), 36.8 (br), 45.7 (br), 53.3 (q), 122.3 (br), 124.0 (br), 128.3 (q (80%)+septet (20%), q: J=69.9 Hz, septet: J=23.2 Hz), 135.7 (d).

Melting point: Below 0° C.

Example 4

Synthesis of N-n-butyl-2-picolinium tricyanomethoxyborate (ionic liquid)

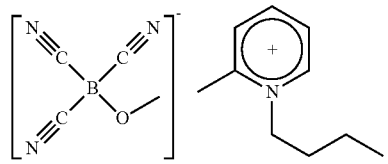

A solution of N-n-butyl-2-picolinium chloride (5.0 g, 27 mmol) in water (20 ml) and K[B(CN)$_3$(OCH$_3$)] (4.3 g, 27 mmol) were mixed with methylene chloride (53 g) and stirred at room temperature for 5 hours. After separation of the aqueous and the organic phase, the latter was washed with 10 ml of water, dried over potassium carbonate and finally evaporated on a rotary evaporator yielding 4.0 g (55%) of N-n-butyl-2-picolinium tricyanomethoxyborate as a low-viscosity liquid.

$^1$H-NMR (500 MHz, CD$_3$CN, TMS): δ [ppm]=0.92 (t, J=7.3 Hz, 3H), 1.35-1.43 (m, 2H), 1.79-1.83 (m, 2H), 2.74 (s, 3H), 3.15 (q, J$_{H/B}$=3.9 Hz, 3H), 4.39 (br t, J=8 Hz, 2H), 7.76-7.82 (m, 2H), 8.26-8.30 (m, 1H), 8.52-8.54 (m, 1H).

$^{13}$C-NMR (125 MHz, CD$_3$CN, TMS): δ [ppm]=12.9 (q), 19.4 (q), 19.7 (t), 31.7 (t), 52.5 (q), 58.0 (t), 126.0 (d), 128.0 (q (80%)+septet (20%), q: J=69.9 Hz, septet: J=20.7 Hz), 130.5 (d), 145.1 (d), 145.3 (d), 155.61 (s).

Melting point: Below 0° C.

Example 5

Synthesis of Tetraethylammonium Tricyanomethoxyborate (Ionic Liquid)

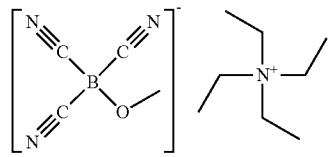

A solution of tetraethylammonium chloride (5.0 g, 30 mmol) in water (22 ml) and K[B(CN)$_3$(OCH$_3$)] (4.8 g, 30 mmol) were mixed with methylene chloride (59 g) and stirred at room temperature for 5 hours. After separation of the aqueous and the organic phase, the latter was washed with 10 ml of water, dried over potassium carbonate and finally evaporated on a rotary evaporator yielding 4.0 g (53%) of tetraethylammonium tricyanomethoxyborate as a low-viscosity liquid.

$^1$H-NMR (500 MHz, CD$_3$CN, TMS): δ [ppm]=1.16 (tt, J=7.3, J$_{H/N}$=1.9 Hz, 12H), 3.12 (q, J=7.3 Hz, 8H), 3.16 (J$_{H/B}$=3.4 Hz, 3H).

$^{13}$C-NMR (125 MHz, CD$_3$CN, TMS): δ [ppm]=6.8 (q), 52.3 (dt, J$_{C/N}$=3.2 Hz), 54.5 (q), 128.0 (q (80%)+septet (20%), q: J=70 Hz, septet: J=23.5 Hz).

Melting range (DSC): Between 1 and 26° C.

Example 6

Synthesis of Tetrabutylphosphonium Tricyanomethoxyborate (Ionic Liquid)

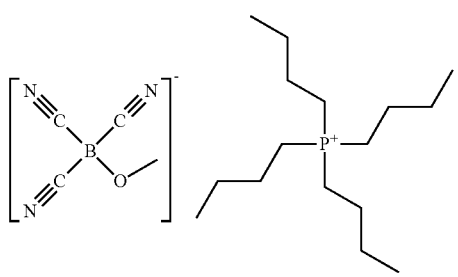

A solution of tetrabutylphosphonium methanesulfonate (5.0 g, 14 mmol) in water (10.4 ml) and K[B(CN)$_3$(OCH$_3$)] (2.2 g, 14 mmol) were mixed with methylene chloride (27.6 g) and stirred at room temperature for 5 hours. After separation of the aqueous and the organic phase, the latter was washed with 10 ml of water, dried over potassium carbonate and finally evaporated on a rotary evaporator yielding 3.4 g (64%) of tetrabutylphosphonium tricyanomethoxyborate as a low-viscosity liquid.

$^1$H-NMR (500 MHz, CD$_3$CN, TMS): δ [ppm]=0.95 (t, J=7.3 Hz, 12H), 1.44-1.53 (m, 16H), 2.04-2.10 (m, 8H), 3.21 ($J_{H/B}$=3.4 Hz, 3H).

$^{13}$C-NMR (125 MHz, CD$_3$CN, TMS): δ [ppm]=13.76 (br q), 19.2 (td, $J_{P/C}$=48.3 Hz), 24.1 (td, $J_{P/C}$=4.6 Hz), 24.7 (td, $J_{P/C}$=15.6), 53.4 (q), 128.0 (q+m, q: J=70 Hz).

Melting point: Below 0° C.

The invention claimed is:

1. A tricyanoborate of formula

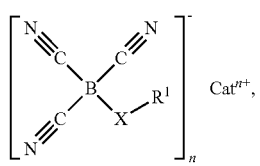

(I)

wherein
R$^1$ is C$_{1-6}$ alkyl, C$_{2-6}$ alkenyl, C$_{6-10}$ aryl or benzyl,
X is oxygen or sulfur, and
Cat$^{n+}$ is a cation with n being 1 or 2, which is selected from the group consisting of an inorganic cation and an organic cation.

2. The tricyanoborate according to claim 1, wherein X is oxygen.

3. The tricyanoborate according to claim 1, wherein R$^1$ is methyl, ethyl or propyl.

4. The tricyanoborate according to claim 3, wherein R$^1$ is methyl.

5. The tricyanoborate according to claim 1, wherein Cat$^{n+}$ is an inorganic cation selected from the group consisting of Li$^+$, Na$^+$, K$^+$, Rb$^+$, Cs$^+$, NH$_4^+$, Be$^{2+}$, Mg$^{2+}$, Ca$^{2+}$, Sr$^{2+}$ and Ba$^{2+}$.

6. The tricyanoborate according to claim 1, wherein Cat$^{n+}$ is an organic cation containing at least one heteroatom selected from the group consisting of nitrogen, phosphorus, sulfur and oxygen.

7. The tricyanoborate according to claim 6, wherein the organic cation is selected from the group consisting of cations of formula
(a) (WR$^2$R$^3$R$^4$R$^5$)$^+$, wherein W is nitrogen or phosphorus, and
 (i) wherein R$^2$ to R$^4$ are, independently, C$_{1-20}$ alkyl, and R$^5$ is C$_{1-20}$ alkyl, C$_{3-10}$ cycloalkyl or C$_{6-10}$ aryl, wherein optionally R$^2$ to R$^5$, independently, contain one or more halogens, or
 (ii) wherein R$^2$ and R$^3$ together with W form a 5- to 7-membered ring and R$^4$ and R$^5$ are, independently, C$_{1-20}$ alkyl, wherein optionally R$^4$ and R$^5$, independently, contain one or more halogens, or
 (iii) wherein R$^2$ and R$^3$ or R$^4$ and R$^5$ in each case together with W form a 5- to 7-membered ring, or
(b) (XR$^6$R$^7$R$^8$)$^+$, wherein X is nitrogen and R$^6$ and R$^7$ together with X form a ring in which X formally has one single bond and one double bond to R$^6$ and R$^7$, and R$^8$ is C$_{1-20}$ alkyl, C$_{3-10}$ cycloalkyl or C$_{6-10}$ aryl, wherein R$^8$ optionally contains one or more halogens, or
(c) (YR$^9$R$^{10}$R$^{11}$)$^+$, wherein Y is sulfur and
 (i) wherein R$^9$ and R$^{10}$ are, independently, C$_{1-20}$ alkyl and R$^{11}$ is C$_{1-20}$ alkyl, C$_{3-10}$ cycloalkyl or C$_{6-10}$ aryl, wherein optionally R$^9$ to R$^{11}$, independently, contain one or more halogens, or
 (ii) wherein R$^9$ and R$^{10}$ together with Y form a 5- to 7-membered ring and R$^{11}$ is C$_{1-20}$ alkyl, C$_{3-10}$ cycloalkyl or C$_{6-10}$ aryl, wherein R$^{11}$ optionally contains one or more halogens, or
(d) (ZR$^{12}$R$^{13}$)$^+$, wherein Z is oxygen or sulfur and R$^{12}$ and R$^{13}$ together with Z form a ring in which Z formally has one single bond and one double bond to R$^{12}$ and R$^{13}$, and
wherein optionally one or more substituents selected from the group consisting of C$_{1-20}$ alkyl, C$_{1-20}$ alkoxy, C$_{3-10}$ cycloalkyl, C$_{6-10}$ aryl, halogen and cyano are bound to each of the rings formed with the substituents R$^2$ to R$^{13}$, wherein optionally the C$_{1-20}$ alkyl, the C$_{1-20}$ alkoxy, the C$_{3-10}$ cycloalkyl and the C$_{6-10}$ aryl, independently, contain one or more halogens, and
wherein optionally each of the rings formed with the substituents R$^2$ to R$^{13}$ contains one or two further, substituted or unsubstituted heteroatoms selected from the group consisting of nitrogen, sulfur and oxygen and/or be fused to another aromatic or non-aromatic 5- to 7-membered ring.

8. The tricyanoborate according to claim 6, wherein the organic cation is selected from the group consisting of organic ammonium, phosphonium, sulfonium, pyrrolidinium, pyrrolinium, pyrrolium, pyrazolium, imidazolium, triazolium, oxazolium, thiazolium, piperidinium, piperazinium, morpholinium, pyridinium, pyridazinium, pyrimidinium, pyrazinium, 1,3-dioxolium, pyrylium and thiopyrylium cation.

9. The tricyanoborate according to claim 6, wherein the organic cation is selected from the group consisting of

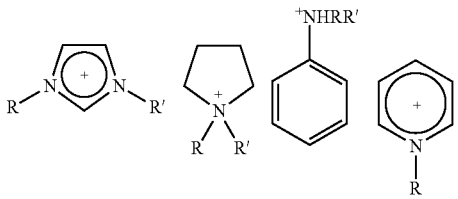

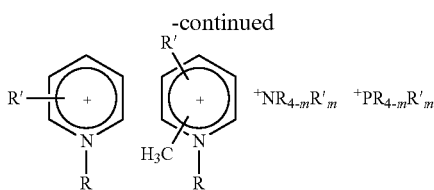

wherein R and R' are, independently, $C_{1-20}$ alkyl, and m is an integer from 0 to 4.

10. The tricyanoborate according to claim 9, wherein the organic cation is of formula

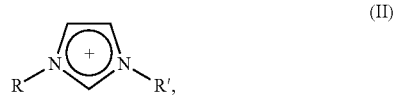

(II)

wherein R and R' are, independently, $C_{1-20}$ alkyl.

11. The tricyanoborate according to claim 10, wherein R is methyl and R' is ethyl.

12. A process for preparing the tricyanoborate as defined in claim 5, comprising reacting characterized in that $B(XR^1)_3$ with a cyanotri-$C_{1-6}$-alkylsilane in the presence of $M^{n+}(CN^-)_n$,
wherein
$R^1$ is $C_{1-6}$ alkyl, $C_{2-6}$ alkenyl, $C_{6-10}$ aryl or benzyl,
X is oxygen or sulfur, and
$M^{n+}$ is an inorganic cation with n being 1 or 2, selected from the group consisting of $Li^+$, $Na^+$, $K^+$, $Rb^+$, $Cs^+$, $NH_4^+$, $Be^{2+}$, $Mg^{2+}$, $Ca^{2+}$, $Sr^{2+}$ and $Ba^{2+}$.

13. A process for preparing the tricyanoborate as defined in claim 6 comprising reacting a tricyanoborate of formula (I)

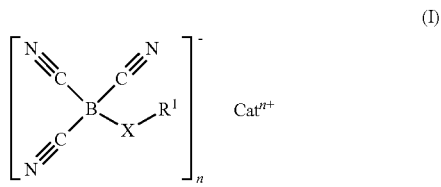

(I)

with a salt of formula $(Q^{n+})_p (Y^{p-})_n$,
wherein
$R^1$ is $C_{1-6}$ alkyl, $C_{2-6}$ alkenyl, $C_{6-10}$ aryl or benzyl,
X is oxygen or sulfur,
$Cat^{n+}$ is an inorganic cation selected from the group consisting of $Li^+$, $Na^+$, $K^+$, $Rb^+$, $Cs^+$, $NH_4^+$, $Be^{2+}$, $Mg^{2+}$, $Ca^{2+}$, $Sr^{2+}$ and $Ba^{2+}$,
$Q^{n+}$ is an organic cation containing at least one heteroatom selected from the group consisting of nitrogen, phosphorus, sulfur and oxygen,
n is 1 or 2,
$Y^{p-}$ is an anion selected from the group consisting of halides, pseudohalides, sulfate and organic acid anions, and
p is 1 or 2.

14. The process according to claim 13, wherein the tricyanoborate that is reacted with a salt of formula $(Q^{n+})_p(Y^{p-})_n$ is prepared precedent according to the process of reacting $B(XR^1)_3$ with a cyanotri-$C_{1-6}$-alkylsilane in the presence of $M^{n+}(CN^-)_n$, wherein
$R^1$ is $C_{1-6}$ alkyl, $C_{2-6}$ alkenyl, $C_{6-10}$ aryl or benzyl,
X is oxygen or sulfur, and
$M^{n+}$ is an inorganic cation with n being 1 or 2, selected from the group consisting of $Li^+$, $Na^+$, $K^+$, $Rb^+$, $Cs^+$, $NH_4^+$, $Be^{2+}$, $Mg^{2+}$, $Ca^{2+}$, $Sr^{2+}$ and $Ba^{2+}$.

15. The tricyanoborate according to claim 2, wherein $R^1$ is methyl, ethyl or propyl.

16. The tricyanoborate according to claim 15, wherein $R^1$ is methyl.

17. The tricyanoborate according to claim 2, wherein $Cat^{n+}$ is an inorganic cation selected from the group consisting of $Li^+$, $Na^+$, $K^+$, $Rb^+$, $Cs^+$, $NH_4^+$, $Be^{2+}$, $Mg^{2+}$, $Ca^{2+}$, $Sr^{2+}$ and $Ba^{2+}$.

18. The tricyanoborate according to claim 3, wherein $Cat^{n+}$ is an inorganic cation selected from the group consisting of $Li^+$, $Na^+$, $K^+$, $Rb^+$, $Cs^+$, $NH_4^+$, $Be^{2+}$, $Mg^{2+}$, $Ca^{2+}$, $Sr^{2+}$ and $Ba^{2+}$.

19. The tricyanoborate according to claim 4, wherein $Cat^{n+}$ is an inorganic cation selected from the group consisting of $Li^+$, $Na^+$, $K^+$, $Rb^+$, $Cs^+$, $NH_4^+$, $Be^{2+}$, $Mg^{2+}$, $Ca^{2+}$, $Sr^{2+}$ and $Ba^{2+}$.

20. The tricyanoborate according to claim 2, wherein $Cat^{n+}$ is an organic cation containing at least one heteroatom selected from the group consisting of nitrogen, phosphorus, sulfur and oxygen.

21. The tricyanoborate according to claim 3, wherein $Cat^{n+}$ is an organic cation containing at least one heteroatom selected from the group consisting of nitrogen, phosphorus, sulfur and oxygen.

22. The tricyanoborate according to claim 4, wherein $Cat^{n+}$ is an organic cation containing at least one heteroatom selected from the group consisting of nitrogen, phosphorus, sulfur and oxygen.

23. The tricyanoborate according to claim 7, wherein X is oxygen.

24. The tricyanoborate according to claim 7, wherein $R^1$ is methyl, ethyl or propyl.

25. The tricyanoborate according to claim 7, wherein $R^1$ is methyl.

26. The tricyanoborate according to claim 7, wherein the organic cation is selected from the group consisting of organic ammonium, phosphonium, sulfonium, pyrrolidinium, pyrrolinium, pyrrolium, pyrazolium, imidazolium, triazolium, oxazolium, thiazolium, piperidinium, piperazinium, morpholinium, pyridinium, pyridazinium, pyrimidinium, pyrazinium, 1,3-dioxolium, pyrylium and thiopyrylium cation.

27. The tricyanoborate according to claim 7, wherein the organic cation is selected from the group consisting of

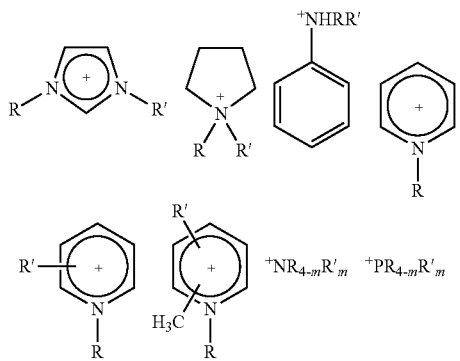

wherein R and R' are, independently, C1-20 alkyl, and m is an integer from 0 to 4.

28. The tricyanoborate according to claim 8, wherein the organic cation is selected from the group consisting of

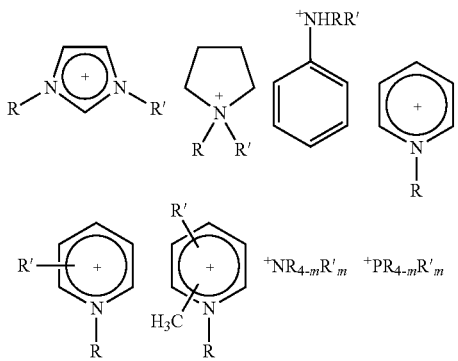

wherein R and R' are, independently, $C_{1-20}$ alkyl, and m is an integer from 0 to 4.

29. The process according to claim 13, wherein the organic cation $Q^{n+}$ is selected from the group consisting of cations of formula
(a) $(WR^2R^3R^4R^5)^+$, wherein W is nitrogen or phosphorus, and
  (i) wherein $R^2$ to $R^4$ are, independently, $C_{1-20}$ alkyl, and $R^5$ is $C_{1-20}$ alkyl, $C_{3-10}$ cycloalkyl or $C_{6-10}$ aryl, wherein optionally $R^2$ to $R^5$, independently, contain one or more halogens, or
  (ii) wherein $R^2$ and $R^3$ together with W form a 5- to 7-membered ring and $R^4$ and $R^5$ are, independently, $C_{1-20}$ alkyl, wherein optionally $R^4$ and $R^5$, independently, contain one or more halogens, or
  (iii) wherein $R^2$ and $R^3$ or $R^4$ and $R^5$ in each case together with W form a 5- to 7-membered ring, or
(b) $(XR^6R^7R^8)^+$, wherein X is nitrogen and $R^6$ and $R^7$ together with X form a ring in which X formally has one single bond and one double bond to $R^6$ and $R^7$, and $R^8$ is $C_{1-20}$ alkyl, $C_{3-10}$ cycloalkyl or $C_{6-10}$ aryl, wherein $R^8$ optionally contains one or more halogens, or
(c) $(YR^9R^{10}R^{11})$, wherein Y is sulfur and
  (i) wherein $R^9$ and $R^{10}$ are, independently, $C_{1-20}$ alkyl and $R^{11}$ is $C_{1-20}$ alkyl, $C_{3-10}$ cycloalkyl or $C_{6-10}$ aryl, wherein optionally $R^9$ to $R^{11}$, independently, contain one or more halogens, or
  (ii) wherein $R^9$ and $R^{10}$ together with Y form a 5- to 7-membered ring and $R^{11}$ is $C_{1-20}$ alkyl, $C_{3-10}$ cycloalkyl or $C_{6-10}$ aryl, wherein $R^{11}$ optionally contains one or more halogens, or
(d) $(ZR^{12}R^{13})^+$, wherein Z is oxygen or sulfur and $R^{12}$ and $R^{13}$ together with Z form a ring in which Z formally has one single bond and one double bond to $R^{12}$ and $R^{13}$, and wherein optionally one or more substituents selected from the group consisting of $C_{1-20}$ alkyl, $C_{1-20}$ alkoxy, $C_{3-10}$ cycloalkyl, $C_{6-10}$ aryl, halogen and cyano are bound to each of the rings formed with the substituents $R^2$ to $R^{13}$, wherein optionally the $C_{1-20}$ alkyl, the $C_{1-20}$ alkoxy, the $C_{3-10}$ cycloalkyl and the $C_{6-10}$ aryl, independently, contain one or more halogens, and wherein optionally each of the rings formed with the substituents $R^2$ to $R^{13}$ contains one or two further, substituted or unsubstituted heteroatoms selected from the group consisting of nitrogen, sulfur and oxygen and/or be fused to another aromatic or non-aromatic 5- to 7-membered ring.

30. The process according to claim 13, wherein the organic cation $Q^{n+}$ is selected from the group consisting of organic ammonium, phosphonium, sulfonium, pyrrolidinium, pyrrolinium, pyrrolium, pyrazolium, imidazolium, triazolium, oxazolium, thiazolium, piperidinium, piperazinium, morpholinium, pyridinium, pyridazinium, pyrimidinium, pyrazinium, 1,3-dioxolium, pyrylium and thiopyrylium cation.

31. The process according to claim 13, wherein the organic cation $Q^{n+}$ is selected from the group consisting of

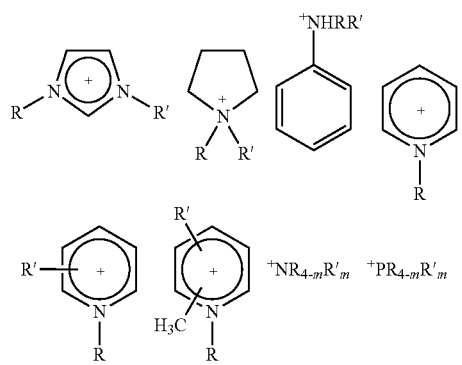

wherein R and R' are, independently, $C_{1-20}$ alkyl, and m is an integer from 0 to 4.

32. The process according to claim 31, wherein the organic cation $Q^{n+}$ is of formula

(II)

wherein R and R' are, independently, $C_{1-20}$ alkyl.

33. The process according to claim 32, wherein R is methyl and R' is ethyl.

* * * * *

UNITED STATES PATENT AND TRADEMARK OFFICE
CERTIFICATE OF CORRECTION

| | | |
|---|---|---|
| PATENT NO. | : 8,283,497 B2 | Page 1 of 1 |
| APPLICATION NO. | : 13/147416 | |
| DATED | : October 9, 2012 | |
| INVENTOR(S) | : Wolfgang Wenger and Cornelia Zur Taschler | |

It is certified that error appears in the above-identified patent and that said Letters Patent is hereby corrected as shown below:

Claim 12, Column 11, line 25, delete "characterized in that";

Claim 27, Column 13, line 1, delete "C1-20 alkyl" and insert --$C_{1-20}$alkyl--;

Signed and Sealed this
Eighteenth Day of December, 2012

David J. Kappos
*Director of the United States Patent and Trademark Office*